(12) United States Patent
Cadix et al.

(10) Patent No.: US 9,617,503 B2
(45) Date of Patent: Apr. 11, 2017

(54) METHOD FOR MODIFYING THE PROPERTIES OF AN AQUEOUS SUSPENSION

(75) Inventors: Arnaud Cadix, Saint-Ouen (FR);
Chi-Thanh Vuong, Lognes (FR);
Bruno Langlois, Paris (FR);
Marie-Pierre Labeau, Burlington, NJ (US)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 12/658,119

(22) Filed: Feb. 3, 2010

(65) Prior Publication Data

US 2010/0210724 A1   Aug. 19, 2010

Related U.S. Application Data

(60) Provisional application No. 61/206,809, filed on Feb. 4, 2009.

(51) Int. Cl.
| | | |
|---|---|---|
| *C09K 8/32* | (2006.01) | |
| *C11D 3/37* | (2006.01) | |
| *A61K 8/04* | (2006.01) | |
| *A61K 8/81* | (2006.01) | |
| *A61K 8/86* | (2006.01) | |
| *A61K 8/90* | (2006.01) | |
| *A61Q 5/02* | (2006.01) | |
| *A61Q 5/12* | (2006.01) | |
| *A61Q 19/10* | (2006.01) | |

(52) U.S. Cl.
CPC ............ *C11D 3/3796* (2013.01); *A61K 8/044* (2013.01); *A61K 8/8152* (2013.01); *A61K 8/8158* (2013.01); *A61K 8/86* (2013.01); *A61K 8/90* (2013.01); *A61Q 5/02* (2013.01); *A61Q 5/12* (2013.01); *A61Q 19/10* (2013.01); *A61K 2800/48* (2013.01); *C09K 2208/00* (2013.01)

(58) Field of Classification Search
CPC ........ E21B 47/00; E21B 47/12; E21B 49/081; E21B 17/02; E21B 17/042; E21B 19/006; E21B 19/06; E21B 19/16; E21B 2049/085; E21B 21/065; E21B 33/038; E21B 33/1208; E21B 33/128; E21B 33/1285; E21B 29/02; E21B 31/00; E21B 31/107; E21B 33/00; E21B 33/0422; E21B 33/068; E21B 33/10; E21B 33/127; E21B 33/1293; E21B 33/13; E21B 33/138; E21B 33/14; E21B 34/045; E21B 34/066; E21B 34/01; E21B 43/006; E21B 43/267; C09K 3/1436; C09K 3/1463; C09K 3/1472; C09K 8/035; C09K 8/512; C09K 8/5756; C09K 8/685; C09K 8/805; C09K 8/32

USPC ........................ 507/200; 514/556; 252/182.3
See application file for complete search history.

(56) References Cited

U.S. PATENT DOCUMENTS

| | | | |
|---|---|---|---|
| 4,585,846 A | 4/1986 | Schulz et al. | |
| 4,607,076 A | 8/1986 | Schulz et al. | |
| 4,708,998 A | 11/1987 | Schulz et al. | |
| 4,788,247 A | 11/1988 | Schulz et al. | |
| 4,822,847 A * | 4/1989 | Schulz ................... | C08F 226/02 524/547 |
| 5,153,289 A | 10/1992 | Schulz et al. | |
| 6,284,854 B1 | 9/2001 | Bowers et al. | |
| 6,313,246 B1 * | 11/2001 | Carter ...................... | C02F 1/56 524/140 |
| 6,410,671 B1 * | 6/2002 | Argillier et al. ............... | 526/306 |
| 6,590,051 B1 | 7/2003 | Carter et al. | |
| 7,956,012 B2 * | 6/2011 | Gupta et al. .................. | 507/120 |
| 2003/0155122 A1 | 8/2003 | Chang et al. | |
| 2006/0217285 A1 | 9/2006 | Destarac | |

FOREIGN PATENT DOCUMENTS

| | | |
|---|---|---|
| WO | 99/03895 | 1/1999 |
| WO | 00/01746 | 1/2000 |
| WO | 01/04201 A1 | 1/2001 |

OTHER PUBLICATIONS

Input Patent Family for WO 00/017146 from http://worldwide.espacenet.com.

* cited by examiner

*Primary Examiner* — Kumar R Bhushan

(57) ABSTRACT

A method for modifying the properties of a suspension of solid or liquid particles in an aqueous medium, includes the step of adding to the suspension or to the aqueous medium a polymer prepared by inverse emulsion polymerization of monomers $A_b$, comprising a betaine group, and of nonionic monomers $B_a$ included in an aqueous phase dispersed in the form of droplets in a hydrophobic external phase, wherein the molar ratio of the monomers $A_b$ to the monomers $B_a$ is from about 4/96 to about 40/60, the polymer exhibits an intrinsic viscosity of greater than 600 mL/g, the reduced specific viscosity being measured by dissolving the polymer in a 20% by weight aqueous NaCl solution.

22 Claims, No Drawings

METHOD FOR MODIFYING THE PROPERTIES OF AN AQUEOUS SUSPENSION

This application claims the benefit of U.S. Provisional Application Ser. No. 61/206,809, filed Feb. 4, 2009.

The present invention is directed to a method for modifying certain physicochemical properties of a suspension of solid or liquid particles in an aqueous medium.

Another subject-matter of the present invention is water-soluble zwitterionic polymers and their use as agents for modifying certain physicochemical properties of an aqueous medium and as agents for modifying surface properties of solid or liquid particles in suspension in the aqueous medium.

Industry uses numerous rheology-modifying agents, in particular thickening agents, in varied compositions. These agents are generally chosen so as to be able to thicken a given composition and to confer, on the composition, a specific newtonian or nonnewtonian rheological behaviour, such as, for example, a certain threshold, a viscoelasticity, a thixotropy, a shear-thinning behaviour, a heat-thickening behaviour, and the like.

The use is frequently made, among thickening agents, of polymers. A great variety of polymers exists and the choice is generally made of a polymer suited to the composition whose rheology is to be modified, in order to confer the desired properties on it, if appropriate by physical and/or chemical interaction with other compounds. In cosmetic compositions, many polymers are thus used to confer, on the compositions, an appropriate stability and/or a viscosity and a texture which are appreciated by consumers. Some compositions can also exhibit a high ionic strength and/or comprise a large amount of salts. In the construction and civil engineering field, attempts are often made to modify the viscosity of compositions or fluids, in particular in underground uses, where the presence of liquids may be a hindrance, in particular in tunnel construction, digging and/or excavation operations. The fluids to be treated may exhibit a high ionic strength and/or comprise relatively large amounts of salts: they can in particular be based on seawater or brines.

There thus exists a constant need for polymers which can vary the rheological properties of different fluids, in particular in the presence of salts and/or at a relatively high ionic strength. It is noted that it is generally important for the polymers to be stable in the fluid or of controllable stability, that is to say for them not to separate from the other constituents, so that in particular the rheological properties are retained for the desired time. It is also noted that it is sometimes important for the rheological properties to be obtained under specific conditions, for example under severe conditions of temperature and/or pressure.

The polymers also used in water-based fluids are acrylamide or methacrylamide polymers, generally acrylamide/acrylate polymers obtained by copolymerization of acrylamide and acrylate or by hydrolysis of polyacrylamide.

However, these polymers are sensitive to the operating and use conditions. A high shear gradient or a high temperature at the bottom of the well result in a decrease in the viscosifying power. Furthermore, they are sensitive to media of high ionic strength as a result of the presence of carboxylate or sulphonate groups, which also result in a loss of their viscosifying power, even precipitation of the molecules in media highly concentrated in divalent ions.

Polyampholytes carrying both positive charges and negative charges, part of which is formed by water-soluble zwitterionic polymers, can be adapted for applications in saline medium. They are generally more soluble and exhibit greater viscosities in saline medium than in deionized water. The reference is then to antipolyelectrolyte behaviour for this type of polymer. However, they may exhibit an inadequate resistance to the salinity of the aqueous medium to be treated or to the shear and temperature conditions of use in the medium and a specific object of the present invention is to provide such zwitterionic polymers which do not exhibit the above disadvantages or which exhibit them in a reduced form. Another specific subject-matter of the present invention is their uses in the aqueous medium.

Polymers comprising units comprising a betaine group are known. The document U.S. Pat. No. 4,788,247 describes terpolymers of units deriving from a sulphobetaine, of units deriving from acrylamide (AM) and of hydrophobic units deriving from an ethoxylated alkyl acrylate. The polymerization is carried out in the presence of large amounts of surfactant (SDS) not making possible the production of groups of the hydrophobic units. Furthermore, the polymerization proves to be difficult to reproduce. The terpolymers exhibit thickening effects on saline media.

The documents U.S. Pat. Nos. 4,607,076, 5,153,289, 4,585,846, 4,822,847 and 4,708,998, each describe polymers of units deriving from a sulphobetaine and of units deriving from vinylpyrrolidone (VP). All these units are hydrophilic units. The polymers exhibit thickening effects on saline media.

The document U.S. Pat. No. 6,284,854 describes polymers formed of 10 to 50 mol % of units deriving from sulphobetaines and 50 to 90 mol % of hydrophobic units. These polymers are used as biocompatible coatings. The polymerizations are carried out in solution, which does not make possible the production of groups of the hydrophobic units.

The document WO 99/03895 describes a process for the micellar polymerization of certain monomers. The process comprises the preliminary preparation of an initial charge comprising hydrophilic monomers and micelles of hydrophobic monomers. Then a solution of initiator and another solution comprising other hydrophilic monomers and micelles of hydrophobic monomers are added continuously.

WO 01/04201 describes in particular polymers of acrylamide and of sulphobetaines prepared by inverse polymerization and of high molecular weight as additives in the paper industry.

WO 00/01746 describes betaine/acrylamide copolymers with a molar mass limited at most to 2,000,000/3,000,000 and comprising a maximum content of betaine monomer of 6%.

There still exists a need for novel polymers exhibiting modified properties, such as:
  good stability at a relatively high ionic strength, in particular a relatively saline medium,
  good thickening power for media comprising a relatively high ionic strength, in particular saline media, indeed even highly saline media,
  good hold of the stability and/or thickening at relatively high temperature, and/or
  a thickening power at low contents of polymer, or
  an improved combination and/or compromise of at least two of these properties.

There also exists a need for processes for the preparation of polymers which are improved and/or which make it possible to obtain polymers exhibiting at least one of the properties mentioned above.

The invention satisfies at least one of the needs expressed above. This is because the present invention has as a subject-matter the use of a zwitterionic polymer as agent for modifying the physicochemical properties of aqueous media and as agent for modifying the surface properties of solid or liquid particles in suspension in an aqueous medium of a polymer comprising a betaine group prepared by inverse emulsion polymerization of monomers $A_b$ comprising a betaine group and of nonionic monomers $B_a$ included in an aqueous phase dispersed in the form of droplets in a hydrophobic external phase, the molar ratio of the monomers $A_b$ to the monomers $B_a$ being between 4/96 and 40/60, more typically between 7/93 and 30/70, the polymers exhibiting an intrinsic viscosity of greater than 600 milliLiters/gram ("mL/g"), more typically of greater than 1000 mL/g, the reduced specific viscosity being measured by dissolving the polymer in a 20% by weight aqueous NaCl solution. The invention also provides uses of such polymers, in particular as rheology-modifying agent, especially as thickening agent, for an aqueous solution, in particular for a solution with a relatively high ionic strength. The invention also relates to a process for modifying, in particular thickening, aqueous compositions, especially those with a relatively high ionic strength, which can comprise in particular salts, by addition of the polymer.

The invention also relates to aqueous compositions comprising the polymer and typically also compounds which increase the ionic strength, in particular salts.

The invention also relates to fluids for the use of the applications targeted by the invention, in particular fluids comprising such polymers and typically also compounds which increase the ionic strength, in particular salts.

In one embodiment, the betaine group-containing monomer $A_b$ comprises, more typically is, one or more monomers selected from following types of monomer compounds:

(a) alkylsulphonates or -phosphonates of dialkylammonioalkyl acrylates or methacrylates, -acrylamides or -methacrylamides, such as, for example:
  (i) sulphopropyldimethylammonioethyl methacrylate, sold by Raschig under the name SPE:

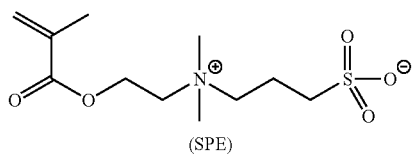 [SMILES: C=C(C)C(=O)OCC[N+](C)(C)CCCS(=O)(=O)[O-]]

(SPE)

(ii) sulphoethyldimethylammonioethyl methacrylate and sulphobutyldimethylammonioethyl methacrylate:

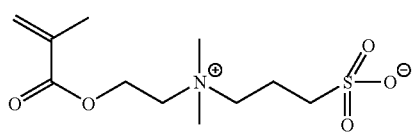

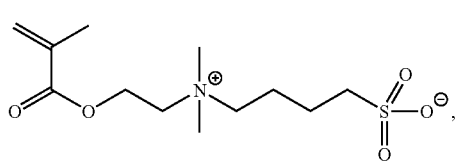

the synthesis of which is described in the paper "Sulfobetaine zwitterionomers based on n-butyl acrylate and 2-ethoxyethyl acrylate: monomer synthesis and copolymerization behavior", Journal of Polymer Science, 40, 511-523 (2002), (iii) sulphohydroxypropyldimethylammonioethyl methacrylate:

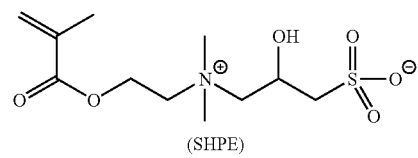 [SMILES: C=C(C)C(=O)OCC[N+](C)(C)CC(O)CS(=O)(=O)O]

(SHPE)

(iv) sulphopropyldimethylammoniopropylacrylamide:

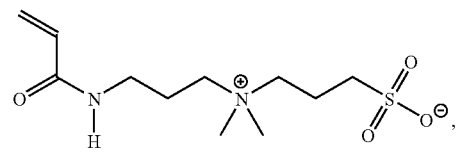 [SMILES: C=CC(=O)NCCC[N+](C)(C)CCCS(=O)(=O)[O-]]

the synthesis of which is described in the paper "Synthesis and solubility of the poly(sulfobetaine)s and the corresponding cationic polymers: 1. Synthesis and characterization of sulfobetaines and the corresponding cationic monomers by nuclear magnetic resonance spectra", Wen-Fu Lee and Chan-Chang Tsai, Polymer, 35 (10), 2210-2217 (1994), (v) sulphopropyldimethylammoniopropylmethacrylamide, sold by Raschig under the name SPP:

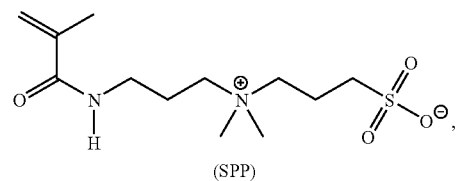

(SPP)

(vi) sulphopropyldimethylammonioethyl methacrylate, sold by Raschig under the name SPDA:

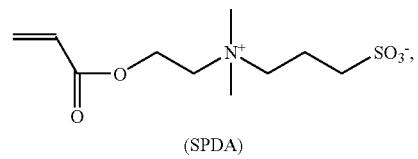

(SPDA)

(vii) sulphohydroxypropyldimethylammoniopropylmethacrylamide:

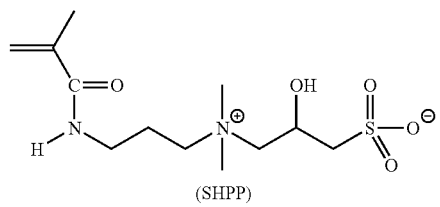 [SMILES: C=C(C)C(=O)NCCC[N+](C)(C)CC(O)CS(=O)(=O)[O-] ; "(SHPP)"]

(SHPP)

(viii) sulphopropyldiethylammonioethyl methacrylate:

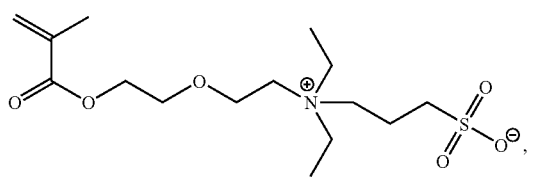 [SMILES: C=C(C)C(=O)OCCOCC[N+](CC)(CC)CCCS(=O)(=O)[O-]]

the synthesis of which is described in the paper "Poly(sulphopropylbetaines): 1. Synthesis and characterization", V. M. Monroy Soto and J. C. Galin, Polymer, 1984, Vol. 25, 121-128, and (ix) sulphohydroxypropyldiethylammonioethyl methacrylate:

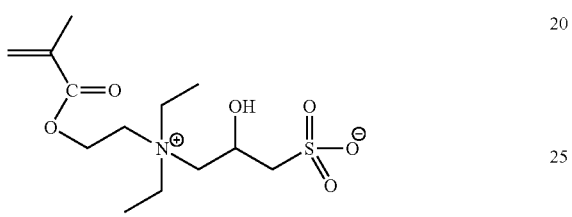

(b) heterocyclic betaine monomers, such as, for example:
  (i) sulphobetaines derived from piperazine, such as, for example:

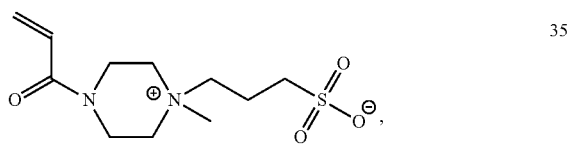

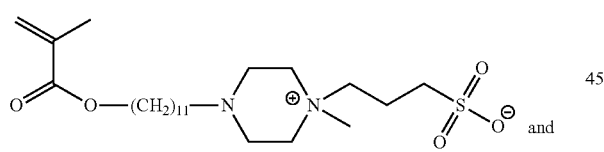

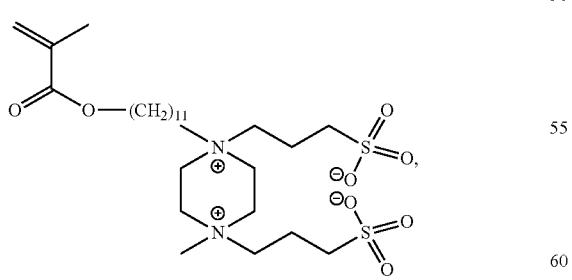

the synthesis of which is described in the paper "Hydrophobically Modified Zwitterionic Polymers: Synthesis, Bulk Properties, and Miscibility with Inorganic Salts", P. Koberle and A. Laschewsky, Macromolecules, 27, 2165-2173 (1994), (ii) sulphobetaines derived from 2-vinylpyridine and 4-vinylpyridine, such as, for example, 2-vinyl-1-(3-sulphopropyl)pyridinium betaine (2SPV or "SPV"):

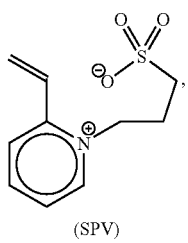

(SPV)

which is sold by Raschig under the name "SPV", and 4-vinyl-1-(3-sulphopropyl)pyridinium betaine (4SPV):

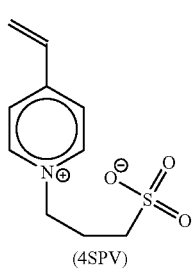

(4SPV)

the synthesis of which is disclosed in the paper "Evidence of ionic aggregates in some ampholytic polymers by transmission electron microscopy", V. M. Casteño and A. E. González, J. Cardoso, O. Manero and V. M. Monroy, J. Mater. Res., 5 (3), 654-657 (1990), and (iv) 1-vinyl-3-(3-sulphopropyl)imidazolium betaine:

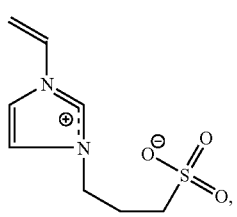

the synthesis of which is described in the paper "Aqueous solution properties of a poly(vinyl imidazolium sulphobetaine)", J. C. Salamone, W. Volkson, A. P. Oison, S. C. Israel, Polymer, 19, 1157-1162 (1978), (c) alkylsulphonates or -phosphonates of dialkylammonioalkylallylics, such as sulphopropylmethyldiallylammonium betaine:

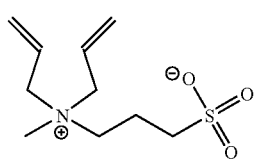

the synthesis of which is described in the paper "New poly(carbobetaine)s made from zwitterionic diallylammonium monomers", Favresse, Philippe; Laschewsky, Andre, Macromolecular Chemistry and Physics, 200 (4), 887-895 (1999), (d) alkylsulphonates or -phosphonates of dialkylammonioalkylstyrenes, such as, for example:

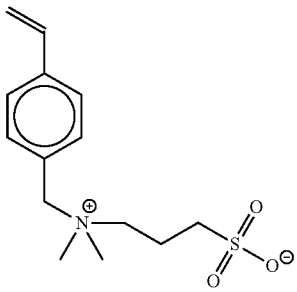

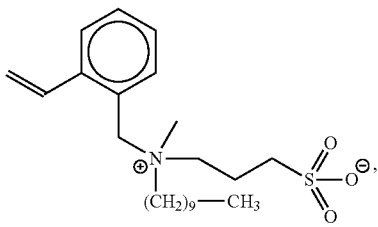

the synthesis of which is described in the paper "Hydrophobically Modified Zwitterionic Polymers: Synthesis, Bulk Properties, and Miscibility with Inorganic Salts", P. Koberle and A. Laschewsky, Macromolecules, 27, 2165-2173 (1994), (e) betaines resulting from ethylenically unsaturated anhydrides and dienes, such as, for example:

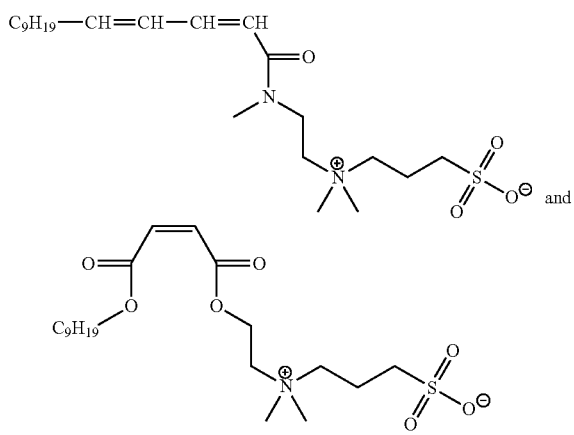

the synthesis of which is described in the paper "Hydrophobically Modified Zwitterionic Polymers: Synthesis, Bulk Properties, and Miscibility with Inorganic Salts", P. Koberle and A. Laschewsky, Macromolecules, 27, 2165-2173 (1994), and (f) phosphobetaines, such as, for example:

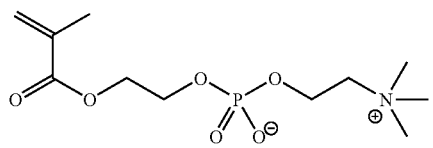

(MPC) or alternatively:

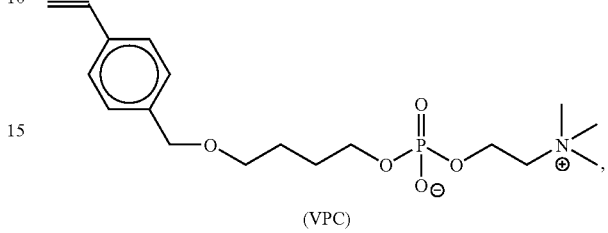

(VPC)

the synthesis of which is described in EP 810239 B1 (Biocompatibles, Alister et al.).

In one embodiment, the betaine group containing monomer comprises, more typically is, one or more monomers selected from monomers according to the formula:

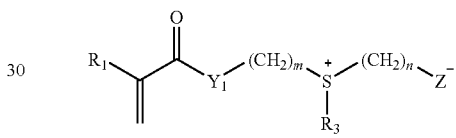

or of formula:

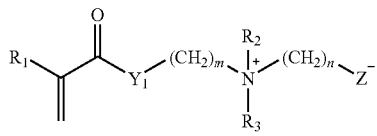

in which:
$R^1$ is hydrogen or methyl,
$R^2$ and $R^3$, which are identical or different, are hydrogen or alkyls having from 1 to 6 carbon atoms,
$Y_1$ is a divalent group of formula —O— or $NR_2$,
$Z^-$ is $SO_3^-$,
m is 2 or 3, and
n is 1-6.

In one embodiment, the monomer $A_b$ comprises, more typically is, one or more monomers selected from the following monomer compounds: sulphopropyldimethylammonioethyl methacrylate (SPE), sulphoethyldimethylammonioethyl methacrylate, sulphobutyldimethylammonioethyl methacrylate, sulphohydroxypropyldimethylammonioethyl methacrylate (SHPE), sulphopropyldimethylammoniopropylacrylamide, sulphopropyldimethylammoniopropylmethacrylamide (SPP), sulphohydroxypropyldimethylammoniopropylmethacrylamide (SHPP), sulphopropyldimethylammonioethyl acrylate (SPDA), sulphopropyldiethylammonioethyl methacrylate, 2-vinyl-1-(3-sulphopropyl)pyridinium betaine, 4-vinyl-1-(3-sulphopropyl)pyridinium betaine, 1-vinyl-3-(3-sulphopropyl)imidazolium betaine, and sulphopropylmethyldiallylammonium betaine.

In one embodiment, the monomer $A_b$ comprises, more typically is, one or more of the following monomer compounds:

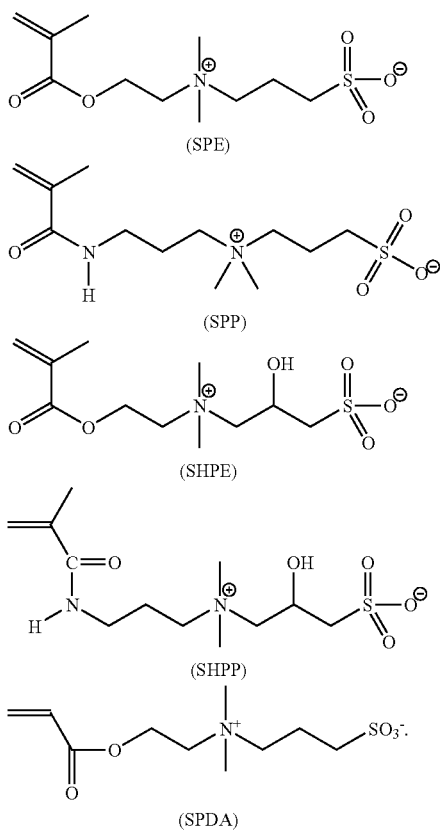

In one embodiment, the nonionic monomers $B_a$ comprises, more typically is, one or more hydrophilic monomers selected from hydroxyethyl acrylate, hydroxyethyl methacrylate, hydroxypropyl acrylate and hydroxypropyl methacrylate, acrylamide (AM), methacrylamide, N-methylolacrylamide, dimethylacrylamide, dimethylmethacrylamide, poly(ethylene oxide), poly(propylene oxide), and copolymers of ethylene oxide and propylene oxide, which copolymers may be in random copolymer or block copolymer form, α-methacrylates, vinyl alcohol, and vinylpyrrolidone.

In one embodiment, the nonionic monomer $B_a$ is acrylamide (AM), and/or the monomer $A_b$ is sulphopropyldimethylammonioethyl methacrylate (SPE) and SPP.

In one embodiment, the polymer is prepared by an inverse polymerization process which comprises the following stages:
  a1): preparation of the inverse emulsion, and
  a2): polymerization.

Stage a1) is carried out by emulsification of a mixture comprising the aqueous phase comprising the monomers, the external phase and at least one emulsifying agent. The polymerization is carried out by bringing together the monomers $A_b$ and optionally the monomers $B_a$ with a compound which generates free radicals and the polymerization is carried out at a temperature between, for example, ambient temperature and 75° C., depending on the initiating system chosen.

The method may be made of any inert hydrophobic liquid, for example aliphatic and aromatic hydrocarbons and halo-carbons, such as toluene, xylene, o-dichlorobenzene, perchloroethylene, hexane, heptane, kerosene, a mineral oil and Isopar M, a substance of isoparaffin type of high purity sold by Exxon Corporation. Likewise, use may be made of any conventional water-in-oil emulsifying agent, such as hexadecyl sodium phthalate, sorbitan monooleate, sorbitan monostearate, mono- and diglycerides, polyethoxylated sorbitol hexaoleate, octyl sodium phthalate or stearyl sodium phthalate. The preferred emulsifying agents are sorbitan monooleate. These emulsifying agents constitute from 0.5% to 10% approximately, typically from 1% to 5% approximately, by weight of the emulsion.

The ratio of the aqueous phase to the oil phase can vary within wide limits. Generally, the water-in-oil emulsions comprise from 20% to 80% approximately of aqueous phase and thus between 80% and 20% approximately of oil phase, these percentages being based on the total weight of the water-in-oil emulsion. A preferred ratio of the aqueous phase to the oil phase is 70 to 75% approximately of the aqueous phase for 30-25% approximately of the oil phase, percentages based on the total weight of the water-in-oil emulsion.

As was said above, the polymerization is initiated by means of a chemical initiator comprising free radicals. This initiator can be dissolved either in the oil phase or in the aqueous phase, according to its solubility characteristics. Mention may be made, as examples of water-soluble initiators, of 4,4'-azobis[4-cyanovaleric acid] (abbreviated to ACVA), potassium persulphate ($K_2S_2O_8$) and t-butyl hydroperoxide.

Mention may be made, as examples of oil-soluble initiators, of azobisisobutyronitrile (AIBN) or 2,2'-azobis(2,4-dimethylvaleronitrile) (ADVN). The method may also be made of water-soluble initiators of redox type, such as bromate/bisulphite or metabisulphite (for example, $KBrO_3$/$NaHSO_3$ or $KBrO_3$/$NaS_2O_5$) or persulphate/bisulphite initiators. The proportion of chemical initiator used depends on several factors. If, thus, it is necessary to maintain a desired reaction rate, the proportion of initiator has to be increased as the reaction temperature falls. By adjusting the reaction temperature and the proportion of initiator, it is possible to carry out the polymerization in a reasonable time and with a reasonable conversion of monomer to polymer, retaining the advantages of a polymerization at low temperatures.

The water-soluble zwitterionic polymers of the present invention can be used in particular as viscosifying agent for aqueous solutions over a wide range of salinity and of temperature and as agent for modifying surfaces of particles in aqueous suspensions.

For these uses/applications, the polymer can be provided in any practical form, for example in the dry solid form or in the vectorized form, for example in the form of a solution or of an emulsion or of a suspension, in particular in the form of an aqueous solution. The vectorized form, for example an aqueous solution, can in particular comprise from 5 to 50% by weight, for example from 10 to 30% by weight, of the polymer.

Water-soluble zwitterionic polymers of this type are also used as fluids in the paint industry as compatibilizing additives; pigments, in cosmetology and paper industry and as treatment agent for clays for the photographic film industry. They are also used as agents for controlling the rheology (viscosifying power) of aqueous suspensions.

The polymer of the invention can advantageously be used in an aqueous composition. The invention also relates to the compositions, typically aqueous compositions, comprising the polymer. The polymer thus makes it possible in particular to increase the viscosity of the compositions. The polymer is in the form of an aqueous composition comprising the inverse emulsion with an aqueous phase comprising the polymer dispersed in the form of droplets in a hydrophobic external phase and other ingredients chosen from a surfactant, an organic salt, an inorganic salt, a detergent and a thickener.

The aqueous composition can additionally comprise ionic entities, such as inorganic salts or organic salts, in particular acid salts, it being possible for the salts to exhibit a surface-active or non-surface-active nature. The composition can in particular be a "saline" composition. The polymer makes it possible in particular to increase the viscosity of compositions comprising ions, in particular of saline compositions, in particular of compositions of relatively high ionic strength, in particular of compositions comprising relatively large amounts of salts, in particular of compositions based on seawater or on brines.

The ionic strength of the composition can be from low to high, depending on the application. It has been found that the polymer can be effective as thickening agent at a zero or low ionic strength and that it can, surprisingly, remain effective at a high ionic strength. The ionic strength can, for example, be at least 0.7 mol/l, indeed even at least 1 mol/l or even greater than 2 mol/l after saturation of the salt or mixture of salts. The composition can in particular comprise at least 35 g/l of a salt. The salts included in the composition can in particular be salts of metals, in particular of alkali metals or alkaline earth metals, which are monovalent, divalent or polyvalent according to the valences available for the metals. They can, for example, be NaCl and/or NaBr and/or $CaCl_2$ and/or $CaBr_2$ and/or $ZnBr_2$ and/or generally more or less complex brines. The composition can in particular be a composition formed of seawater or a brine comprising the polymer.

The composition can in particular comprise at least one surfactant, for example a surfactant employed during the preparation of the polymer. The amount of surfactant can be the amount introduced with the polymer, if a surfactant was used during the preparation of the latter. However, the addition of some is not ruled out. Typically, the composition comprises at least 0.001% by weight, advantageously at least 0.01% or 0.1% by weight, of surfactant, with respect to the polymer.

The total amount of surfactant included in the composition can in particular vary depending upon the use of the composition. The amount can range from the values indicated above to approximately 20%, for example typically from 5% to 15% or 20% for detergent compositions, in particular compositions for caring for the body intended to be rinsed off, such as shampoos and/or shower gels. The amount by weight of polymer in the compositions can depend on the rheological behaviour desired and/or on the thickening strength desired for the compositions and on the possible presence of other compounds, in particular ionic compounds, such as salts. In practice, the amount by weight can in particular be greater than 0.01% by weight, with respect to the composition, for example greater than 0.1% by weight and often greater than or equal to 0.5% or 1% by weight. The amount will generally be less than or equal to 20% by weight, typically 10% by weight. Advantageous thickenings can in particular be observed in ranges from 0.1% to 1% by weight, and/or from 1% to 2% by weight, and/or from 2% to 3% by weight, and/or from 3% to 4% by weight, and/or from 4% to 5% by weight.

In one embodiment, the aqueous composition is a fluid used in civil engineering, in particular for excavating and/or digging operations. In an alternative embodiment, the composition is a composition for household care, in particular a consumable intended to be employed in the private sphere or a product for industrial and/or institutional purposes generally intended to be employed by cleaning services. In another alternative embodiment, the composition is a cosmetic composition, typically intended to be rinsed out, such as a shampoo, a conditioner intended to be rinsed out and/or a shower gel.

In the compositions for household care or in cosmetic compositions in particular, the polymer can provide a viscosity and/or flow properties and/or a texture valued by consumers. In cosmetic compositions comprising structured surfactant phases, the polymer can provide an advantageous excess viscosity.

Finally, it is mentioned that the fluid can be used as fluid for the removal of excavation products, in particular in the sectors of deep level construction, of the execution of tunnels or wells, in civil engineering, or in the mining sector. The excavation products in these applications are suspended in the fluid by introduction of the fluid into the area from where they have to be removed.

The compositions, whatever the field of use, can comprise dispersed liquid particles (emulsified droplets) or dispersed solid particles. Liquid particles can, for example, be synthetic oils (for example silicone oils) or oils of vegetable or mineral origin. The solid particles can in particular be sand, density-modifying particles, debris and/or polymeric particles. The polymer can promote the suspending of these particles during the time necessary for the use of the composition and/or during a storage time. It can also alternatively contribute to easy transportation of the particles, in order to position them at or to move them to an appropriate spot.

It is mentioned that the composition can have a temperature ranging from 20° C. to relatively high temperatures, for example greater than or equal to 50° C., in particular greater than or equal to 70° C., in particular greater than or equal to 100° C., in particular greater than or equal to 150° C. or even greater than or equal to 180° C. The pressure can be atmospheric pressure or a greater pressure. The temperature and the pressure can vary according to the use which is made of the fluid and its environment. The polymer can remain effective under conditions requiring relatively high temperatures, in particular in the fields of oil and/or gas extraction. Thus, the composition can be employed at the temperatures mentioned above.

The reduced specific viscosity is measured by dissolving the polymer in a 20% by weight aqueous NaCl solution. The intrinsic viscosity η is then obtained by linear extrapolation of the reduced specific viscosity to zero concentration of polymer. The slope of this extrapolation is equal to:

$$k'(\eta)^2,$$

wherein k' is the Huggins coefficient. This method of calculating η is described in detail in the publication Polymer Handbook (4$^{th}$ edition), J. Brandrup, E. H. Immergut and E. A. Grulke, Wiley (1999), cited as reference. This specific viscosity makes it possible to have indirect access to the molecular weights of greater than approximately 2,000,000 grams per mole, which cannot be directly determined experimentally.

Other characteristics or advantages of the invention may become apparent in the light of the examples which follow, given by way of illustration without a limiting nature.

EXAMPLE 1 (COMPARATIVE)

Solution Polymerization-poly(acrylamide/SPP) 90/10 mol/mol

Copolymerization:

82.4 g of 50% acrylamide in water, 18.8 g of SPP and 94.4 g of water are added to a 500 ml three-necked round-bottom flask equipped with a nitrogen inlet, a mechanical stirrer (anchor), a reflux condenser and temperature regulation via a thermostatically controlled bath of oil. The temperature of the reaction medium is brought to 65° C. while flushing with nitrogen. 0.3 g of sodium persulphate dissolved in 5 g of water is added at 65° C. The temperature of the reaction medium is maintained for 24 h. The combined mixture is subsequently cooled to ambient temperature. The final product exists in the form of a translucent gel.

The molar mass of the polymer obtained can be conventionally adjusted by modifying the amount of initiator introduced, the reaction temperature or the addition of a transfer agent. The concentrations of initiator and the corresponding molar masses, reported as weight average molecular weight ("Mw"), as determined by steric exclusion chromatography are set forth in Table 1 below:

TABLE 1

| Example | Concentration of initiator with respect to the monomers | Mw by chromatography (kg/mol) |
| --- | --- | --- |
| 1-1 | 0.2% + transfer agent | 63 |
| 1-2 | 5% | 370 |

EXAMPLE 2

Inverse Emulsion Polymerization-poly(acrylamide/SPP) 90/10 mol/mol

The synthesis takes place in two stages: preparation of an emulsion comprising the monomers and the surfactants, followed by copolymerization.

Preparation of an Emulsion Comprising the Monomers and the Surfactants:

110.2 g of Shellsol D80 (Shell Chemicals), 18.5 g of G946 (ICI), 9.3 g of Rhodasurf LA-3 (Rhodia) and 4.9 g of Hypermer B261 (Uniquema) are added to a 250 ml glass beaker with magnetic stirring. Stirring is maintained until a clear solution is obtained (Mixture 1). 199.8 g of 50% acrylamide in water, 91.3 g of 50% SPP in water, 0.2 g of Versene 100 (Dow) and 2.9 g of sodium sulphate are added to a 500 ml glass beaker with magnetic stirring. Stirring is maintained until a clear solution is obtained (Mixture 2). Mixture 2 is subsequently introduced into Mixture 1 with magnetic stirring. Stirring is maintained for 5 min and then all the liquid is added to a mixer of rotor/stator type in order to be mixed for 10 s (6000 revolutions/min). The stable emulsion is thus obtained.

Copolymerization

All the emulsion prepared immediately above is added to a 1 liter jacketed glass reactor equipped with a nitrogen inlet, a mechanical stirrer, a reflux condenser and temperature regulation via a thermostatically controlled bath. The temperature of the reaction medium is brought to 45° C. while flushing with nitrogen. 0.2 g of Trigonox 25C75 (Akzo Nobel) is added at 45° C. An additional 0.2 g of Trigonox 25C75 is added 4 hours after this addition. The temperature of the reaction medium is subsequently brought to 55° C. for 3 h. The combined mixture is cooled to ambient temperature.

The final emulsion exists in the form of a translucent and slightly coloured liquid which is not very viscous.

By following the procedure described above, polymers of variable molar masses are produced by modifying the level of initiator. However, for numerous tests, the molar masses are too high to be measured by steric exclusion chromatography. The molar masses are certainly significantly greater than $3 \times 10^6$ g/mol. Furthermore, copolymers with variable acrylamide/SPP ratios are also synthesized. The characteristics of the products are referenced in Table 2 below:

TABLE 2

| Example | Operating conditions | Mw by chromatography (kg/mol) |
| --- | --- | --- |
| 2-1 | concentration initiator = 0.1 mol % vs monomers, T = 65° C., [Am]/[SPP] = 90/10 mol/mol | 2000 |
| 2-2 | concentration initiator = 0.05 mol % vs monomers, T = 65° C., [Am]/[SPP] = 90/10 mol/mol | not measurable |
| 2-3 | concentration initiator = 0.05 mol % vs monomers, T = 55° C., [Am]/[SPP] = 90/10 mol/mol | not measurable |
| 2-4 | concentration initiator = 0.1 mol % vs monomers, [Am]/[SPP] = 90/10 mol/mol | not measurable |
| 2-5 | concentration initiator = 0.02 mol % vs monomers, [Am]/[SPP] = 90/10 mol/mol | not measurable |
| 2-6 | concentration initiator = 0.1 mol % vs monomers, [Am]/[SPP] = 98/2 mol/mol | not measurable |
| 2-7 | concentration initiator = 0.1 mol % vs monomers, [Am]/[SPP] = 95/5 mol/mol | not measurable |
| 2-8 | concentration initiator = 0.1 mol % vs monomers, [Am]/[SPP] = 80/20 mol/mol | not measurable |
| 2-9 | concentration initiator = 0.1 mol % vs monomers, [Am]/[SPP] = 70/30 mol/mol | not measurable |
| 2-10 | concentration initiator = 0.1 mol % vs monomers, [Am]/[SPP] = 50/50 mol/mol | not measurable |

EXAMPLE 3

Evaluations

The viscosities of the polymer solutions are evaluated using an AR2000 rheometer (TA Instrument, Surrey, United Kingdom) provided with geometry of Couette type (internal radius=14 mm; external radius=15 mm and height=42 mm).

Molar Masses

The viscosity contributed by the dissolution of a polymer is represented by its intrinsic viscosity (the linear extrapolation to zero concentration of the reduced specific viscosity:

$$[\eta] = \lim_{c \to 0} \frac{\eta - \eta_0}{\eta_0 c},$$

where $\eta$ is the viscosity of the solution comprising the polymer, $\eta_0$ is the viscosity of the solvent and c is the concentration of polymer.

The intrinsic viscosity, for a polymer chemical composition under given solvent conditions, is related to the molar mass by the Mark-Houwink relationship (Polymer Handbook ($4^{th}$ edition), J. Brandrup, E. H. Immergut and E. A. Grulke, Wiley (1999)):

$$[\eta] = KM^a$$

wherein K and a are constants which depend on the chemical composition of the polymer and on the solvent and temperature.

The polymers of Examples 1 and 2 are purified and dried and then dissolved in a 20% by weight NaCl solution at different concentrations of polymer. The reduced specific viscosity curves as a function of the polymer concentration make it possible to determine the intrinsic viscosity given in Table 3 below.

TABLE 3

|  | Example | Mw by chromatography (kg/mol) | Intrinsic viscosity (mL/g) |
|---|---|---|---|
| Solution | 1-1 | 63 | 37 |
| Solution | 1-2 | 370 | 112 |
| Inverse emulsion | 2-1 | 2000 | 320 |
| Inverse emulsion | 2-2 | not measurable | 470 |
| Inverse emulsion | 2-3 | not measurable | 550 |
| Inverse emulsion | 2-4 | not measurable | 850 |
| Inverse emulsion | 2-5 | not measurable | 1100 |

Rheology in Saline Solutions

The copolymers described in Examples 1 and 2 are used in the solutions of variable salinities described in Table 4 below.

TABLE 4

| Reference | Composition (w salt per 1 kg of solution) | Density | Viscosity at 25° C. (mPa · s) |
|---|---|---|---|
| $ZnBr_2/CaBr_2$ | $ZnBr_2$ 550 g/$CaBr_2$ 230 g | 2.3 | 25.2 |
| $CaCl_2/CaBr_2$ | $CaCl_2$ 230 g/$CaBr_2$ 330 g | 1.7 | 5.9 |
| 45% NaBr | NaBr 446 g | 1.5 | 2.4 |
| 20% NaCl | NaCl 200 g | 1.15 | 1.48 |
| 10% NaCl | NaCl 100 g | 1.07 | 1.2 |
| 5% NaCl | NaCl 50 g | 1.03 | 1.0 |
| Purified water | / | 0.99 | 0.95 |

The polymers are purified and dried. The powders obtained are dissolved at 10 g/l with magnetic stirring. The viscosities are measured 72 h after the preparation of the samples and the values obtained are collated in Table 5 below.

These results demonstrate that the viscosifying power of the polymers according to the invention increases as the molar mass (i.e. the intrinsic viscosity) increases and as the salinity increases.

Direct Dispersion

The polymers of Example 2, synthesized by inverse emulsion polymerization with the composition Am/SPP (90/10), are dispersed directly in the brines.

5% by weight of surfactant Soprophor 4D384 (Rhodia) are added to the inverse emulsion 5 minutes before mixing with the brines. The amount necessary to obtain 10 g/l of polymer is dispersed in the brines. These preparations are, in a first step, stirred vigorously by hand for a few moments and then stirred with a magnetic bar until they are used.

Relative viscosities at a polymer concentration of 10 g/l are measured here 24 h after the preparation of the samples (gradient of 1 $s^{-1}$ at 25° C.) and the values are collated in Table 6 below.

TABLE 6

| Example | Intrinsic viscosity (mL/g) | Relative viscosity: NaBr | Relative viscosity: $CaCl_2/CaBr_2$ | Relative viscosity: $ZnBr_2/CaBr_2$ |
|---|---|---|---|---|
| 2-1 | 320 | 17 | 25 | 115 |
| 2-2 | 470 | 59 | 110 | 529 |
| 2-3 | 550 | 77 | 217 | 549 |
| 2-4 | 850 | 114 | 437 | 797 |

These results demonstrate that the viscosifying power of the polymers according to the invention is very high in brines highly concentrated in salt.

High-temperature Stability

Solutions of polymers comprising variable levels of SPP are prepared according to the protocol described in Example 2 at a concentration by weight of 0.5% in the brine $ZnBr_2/CaBr_2$.

The viscosities of these solutions are measured after mixing at ambient temperature and then after ageing in pressurized cells (acid digestion bombs—Parr instruments) in a rolling oven at 160° C. for 6 h.

The aged solutions may exhibit solid residues; if appropriate, these solutions are filtered through a 100 μm cloth.

TABLE 5

Relative viscosity at a polymer concentration at 10 g/l (gradient of 1 $s^{-1}$ at 25° C.)

|  | Example | Intrinsic viscosity (mL/g) | Relative viscosity: Purified water | Relative viscosity: 5% NaCl | Relative viscosity: 10% NaCl | Relative viscosity: 20% NaCl |
|---|---|---|---|---|---|---|
| Solution | 1-1 | 37 | 1.3 | 1.5 | 1.3 | 1.4 |
| Solution | 1-2 | 112 | 2.5 | 2.3 | 2.1 | 2.4 |
| Inverse emulsion | 2-1 | 320 | 14 | 10 | 9.2 | 11 |
| Inverse emulsion | 2-2 | 470 | 16 | 18 | 19 | 22 |
| Inverse emulsion | 2-3 | 550 | 51 | 60 | 72 | 82 |
| Inverse emulsion | 2-4 | 850 | 59 | 98 | 102 | 108 |
| Inverse emulsion | 2-5 | 1100 | 100 | 179 | 165 | 196 |

The viscosities are then measured at 90° C. and the values are collated in Table 7 below.

TABLE 7

Relative viscosity at a polymer concentration of 0.5% by weight (gradient of 100 s$^{-1}$ at 90° C.)

| Example | SPP level (mol %) | Relative viscosity: initial solution | Relative viscosity: solutions aged at 160° C. | |
|---|---|---|---|---|
| 2-6 | 2 | 51 | 1.0 | Precipitate |
| 2-7 | 5 | 53 | 1.1 | Precipitate |
| -4 | 10 | 60 | 9.7 | Homogeneous solution |
| 2-8 | 20 | 33 | 8.8 | Homogeneous solution |
| 2-9 | 30 | 13.5 | 11.2 | Homogeneous solution |
| 2-10 | 50 | 5.5 | 4.8 | Homogeneous solution |

These results demonstrate that the high-temperature stability of the polymers according to the invention dissolved in brines is directly related to the level of SPP incorporated in the polymer. In this instance, a minimum level of 10 mol % is necessary to maintain the homogeneity of the solution if the latter is exposed for a long time to high temperatures.

The invention claimed is:

1. A method for modifying the properties of a composition of a suspension of dispersed solid or liquid particles in an aqueous medium, comprising adding a polymer to the composition, increasing the viscosity of the composition and promoting the suspending of the dispersed solid or liquid particles in the aqueous medium,
   wherein said polymer is prepared by inverse emulsion polymerization of monomers $A_b$, comprising a betaine group, and of nonionic monomers $B_a$ included in an aqueous phase dispersed in the form of droplets in a hydrophobic external phase,
   wherein the molar ratio of the monomers $A_b$ to the monomers $B_a$ is from about 4/96 to about 40/60, the polymer exhibits an intrinsic viscosity of greater than 600 milliLiters/gram, the intrinsic viscosity being measured by dissolving the polymer in a 20% by weight aqueous NaCl solution,
   wherein the composition exhibits an ionic strength of at least 0.7 mol/l, and
   wherein the dispersed particles comprise solid particles comprising sand, density-modifying particles, excavation products, debris, or polymeric particles, and/or liquid particles comprising synthetic oils, oils of vegetable origin, or oils of mineral origin,
   wherein the composition of the suspension of dispersed solid or liquid particles in the aqueous medium is at a temperature of greater than or equal to 70° C. wherein the suspension comprises greater than or equal to 0.5% of the polymer; and
   wherein the aqueous medium is a saline composition that comprises at least 35 g/l of a salt.

2. The method according to claim 1, wherein the monomer $A_b$ comprises one or more monomers selected from:
   alkylsulphonates or -phosphonates of dialkylammonioalkyl acrylates or methacrylates, -acrylamides or -methacrylamides,
   heterocyclic betaine monomers,
   alkylsulphonates or -phosphonates of dialkylammonioalkylallylics,
   alkylsulphonates or -phosphonates of dialkylammonioalkylstyrenes,
   betaines resulting from ethylenically unsaturated anhydrides and dienes, and phosphobetaines.

3. The method according to claim 1, wherein the monomer $A_b$ comprises one or more monomers selected from sulphohydroxypropyldiethylammonioethyl methacrylate, sulphobetaines derived from piperazine, 2-vinyl-1-(3-sulphopropyl)pyridinium betaine (2SPV or "SPV"), 4-vinyl-1-(3-sulphopropyl)pyridinium betaine (4SPV), 1-vinyl-3-(3-sulphopropyl)imidazolium betaine, sulphopropylmethyldiallylammonium betaine, alkylsulphonates or phosphonates of dialkylammonioalkylstyrenes, betaines derived from ethylenically unsaturated anhydrides and dienes, and phosphobetaines.

4. The method according to claim 1, wherein the monomer $A_b$ comprises one or more monomers selected from monomers according to the formula:

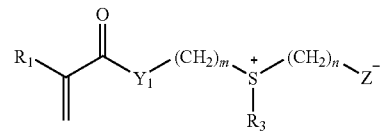

or the formula:

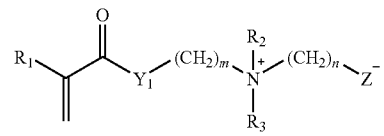

in which:
   $R^1$ is hydrogen or methyl,
   $R^2$ and $R^3$, which are identical or different, are hydrogen or alkyl having from 1 to 6 carbon atoms,
   $Y_1$ is a divalent group of formula —O— or $NR_2$,
   $Z^-$ is $SO_3^-$,
   m is 2 or 3, and
   n is 1-6.

5. The method according claim 1, wherein the monomer $A_b$ comprises one or more monomers selected from:
   sulphopropyldimethylammonioethyl methacrylate (SPE),
   sulphoethyldimethylammonioethyl methacrylate,
   sulphobutyldimethylammonioethyl methacrylate,
   sulphohydroxypropyldimethylammonioethyl methacrylate (SHPE),
   sulphopropyldimethylammoniopropylacrylamide,
   sulphopropyldimethylammoniopropylmethacrylamide (SPP),
   sulphohydroxypropyldimethylammoniopropylmethacrylamide (SHPP),
   sulphopropyldiethylammonioethyl methacrylate,
   2-vinyl-1-(3-sulphopropyl)pyridinium betaine,
   4-vinyl-1-(3-sulphopropyl)pyridinium betaine,
   sulphopropyldimethylammonioethyl methacrylate,
   1-vinyl-3-(3-sulphopropyl)imidazolium betaine, and
   sulphopropylmethyldiallylammonium betaine.

6. The method according to claim 1, wherein the monomer $A_b$ comprises one or more monomers according to the following formulae:

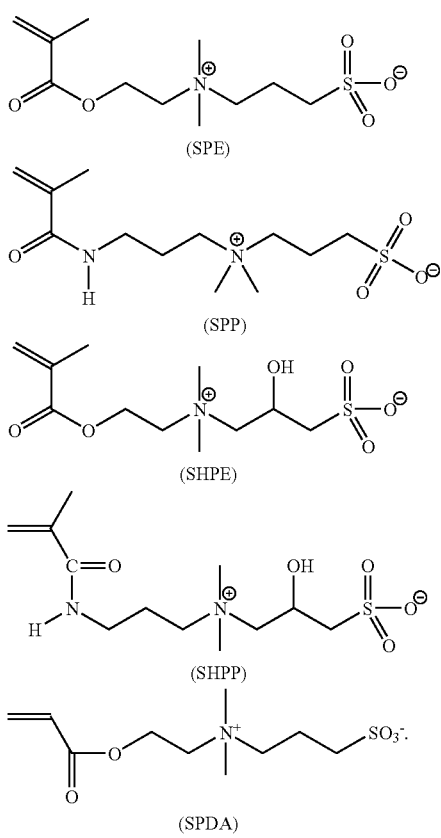

7. The method according to claim 1, wherein, during the polymerization, the monomer $B_a$ is a hydrophilic monomer included in the disperse aqueous phase.

8. The method according to claim 1, wherein the nonionic monomer $B_a$ comprises one or more of hydroxyethyl acrylate, hydroxyethyl methacrylate, hydroxypropyl acrylate, hydroxypropyl methacrylate, glycerol monomethacrylate, acrylamide (AM), methacrylamide, N-methylolacrylamide, dimethylacrylamide, dimethylmethacrylamide, poly(ethylene and/or propylene oxide), if appropriate random or in the block form, α-methacrylates, vinyl alcohol or vinylpyrrolidone.

9. The method according to claim 1, wherein the hydrophilic nonionic monomer $B_a$ comprises acrylamide (AM).

10. The method according to claim 1, wherein the monomer $A_b$ is sulphopropyldimethylammonioethyl methacrylate (SPE) or sulphopropyldimethylammoniopropylmethacrylamide (SPP).

11. The method according to claim 1, wherein the hydrophobic external phase is based on a hydrocarbon.

12. The method according to claim 1, wherein the polymerization comprises the following stages: a1): preparation of the inverse emulsion, and a2): polymerization.

13. The method according to claim 12, wherein stage a1) is carried out by emulsification of a mixture comprising the aqueous phase comprising the monomers, the external phase and at least one emulsifying agent.

14. The method according to claim 12, wherein polymerization is carried out by bringing together monomers $A_b$ and optionally monomers $B_a$ with a compound which generates free radicals.

15. The method according to claim 12, wherein polymerization is carried out at a temperature between ambient temperature and 75° C.

16. The method according to claim 1, wherein the polymer is in the form of an aqueous composition comprising the inverse emulsion with an aqueous phase comprising the polymer dispersed in the form of droplets in a hydrophobic external phase and other ingredients chosen from a surfactant, an organic salt, an inorganic salt, a detergent and a thickener.

17. The method according to claim 1, wherein the saline composition is based on seawater or on a brine.

18. The method according to claim 16, wherein the aqueous composition is a fluid for use in civil engineering for excavating and/or digging operations, a composition for household care, or a cosmetic composition.

19. The method of claim 1, wherein the polymer is effective to promote the suspending of the dispersed solid or liquid particles in the aqueous medium at a temperature of greater than or equal to 100° C.

20. The method of claim 1, wherein the polymer is prepared by inverse emulsion polymerization of at least one monomer Ab comprising sulphopropyldimethylammoniopropylmethacrylamide and one or more nonionic monomers Ba, wherein the amount of sulphopropyldimethylammoniopropylmethacrylamide is at least 10 mole % of the combined amount of monomers Ab and monomers Ba.

21. The method of claim 20, wherein the polymer is effective to promote the suspending of the dispersed solid or liquid particles in the aqueous medium at a temperature of greater than or equal to 150° C.

22. The method of claim 1, wherein the suspension comprises greater than or equal to 1% but less than or equal to 20% by weight of the polymer.

* * * * *